United States Patent
Christophe et al.

(10) Patent No.: US 10,676,730 B2
(45) Date of Patent: Jun. 9, 2020

(54) MUTATED FACTOR X POLYPEPTIDES AND USES THEREOF FOR THE TREATMENT OF HAEMOPHILIA

(71) Applicants: INSERM (INSTITUT NATIONAL DE LA SANTÉ ET DE LA RECHERCHE MÉDICALE), Paris (FR); UNIVERSITÉ PARIS-SUD, Orsay (FR)

(72) Inventors: Olivier Christophe, Le Kremlin-Bicetre (FR); Petrus Lenting, Le Kremlin-Bicetre (FR); Cécile Denis, Le Kremlin-Bicetre (FR)

(73) Assignees: INSERM (INSTITUT NATIONAL DE LA SANTE ET DE LA RECHERCHE MEDICALE), Paris (FR); UNIVERSITE PARIS-SUD, Orsay (FR)

( * ) Notice: Subject to any disclaimer, the term of this patent is extended or adjusted under 35 U.S.C. 154(b) by 0 days.

(21) Appl. No.: 15/542,218

(22) PCT Filed: Jan. 6, 2016

(86) PCT No.: PCT/EP2016/050134
§ 371 (c)(1),
(2) Date: Jul. 7, 2017

(87) PCT Pub. No.: WO2016/110510
PCT Pub. Date: Jul. 14, 2016

(65) Prior Publication Data
US 2017/0369861 A1    Dec. 28, 2017

(30) Foreign Application Priority Data
Jan. 7, 2015 (EP) .................................. 15305010

(51) Int. Cl.
| | | |
|---|---|---|
| *C12N 9/64* | (2006.01) | |
| *C07K 14/75* | (2006.01) | |
| *A61K 38/00* | (2006.01) | |
| *C07K 14/745* | (2006.01) | |

(52) U.S. Cl.
CPC .......... *C12N 9/6432* (2013.01); *C07K 14/745* (2013.01); *C07K 14/75* (2013.01); *C12Y 304/21006* (2013.01); *A61K 38/00* (2013.01)

(58) Field of Classification Search
CPC ...... A61K 38/00; C07K 14/745; C07K 14/75; C12N 9/6432; C12Y 304/21006
See application file for complete search history.

(56) References Cited

FOREIGN PATENT DOCUMENTS

| | | |
|---|---|---|
| EP | 1 728 798 A1 | 12/2006 |
| WO | 2010/070137 A1 | 6/2010 |
| WO | 2014/018120 A1 | 1/2014 |

OTHER PUBLICATIONS

Louvain-Quintard et al., "Thrombin-activable factor X re-establishes an intrinsic amplification in tenase-deficient plasmas", Journal of Biological Chemistry, Dec. 1, 2005, pp. 41352-41359, vol. 280, No. 5, America Society for Biochemistry and Molecular Biology, US.

Quade-Lyssy et al., "Engineered Factor VII, Factor IX, and Factor X Variants for Hemophilia Gene Therapy", Journal of Genetic Syndromes & Gene Therapy, Dec. 10, 2012, pp. 1-7, OMICS Publishing Group, US.

*Primary Examiner* — James H Alstrum-Acevedo
*Assistant Examiner* — Erinne R Dabkowski
(74) *Attorney, Agent, or Firm* — W&C IP

(57) ABSTRACT

The present invention relates to mutated factor (FX) polypeptides and uses thereof for the treatment of haemophilia. In particular, the present invention relates to a mutated factor X (FX) polypeptide wherein the heavy chain comprises at least one mutation selected from the group consisting of: —the mutation which consists of the substitution of the glutamic acid residue (E) at position 255 of Seq. ID No. 1 by a glutamine residue (Q), an asparagine residue (N), a serine residue (S), an alanine residue (A), or a tyrosine residue (Y); —the mutation which consists of the substitution of the glutamic acid residue (E) at position 256 of Seq. ID No. 1 by a glutamine residue (Q); and —the mutation which consists of the substitution of the glutamic acid residue (E) at position 258 of Seq. ID No. 1 by a glutamine residue (Q).

10 Claims, 1 Drawing Sheet
Specification includes a Sequence Listing.

SEQ ID NO:1

| | | | |
|---|---|---|---|
| -40 | Met-Gly-Arg-Pro-Leu-His-Leu-Val-Leu-Leu-Ser-Ala-Ser-Leu-Ala-Gly-Leu-Leu-Leu-Leu | -21 | |
| 1 | | 20 | |
| -20 | Gly-Glu-Ser-Leu-Phe-Ile-Arg-Arg-Glu-Gln-Ala-Asn-Asn-Ile-Leu-Ala-Arg-Val-Thr-Arg | -1 | |
| 21 | | 40 | |
| 1 | Ala-Asn-Ser-Phe-Leu-Glu-Glu-Met-Lys-Lys-Gly-His-Leu-Glu-Arg-Glu-Cys-Met-Glu-Glu | 20 | |
| 41 | | 60 | |
| 21 | Thr-Cys-Ser-Tyr-Glu-Glu-Ala-Arg-Glu-Val-Phe-Glu-Asp-Ser-Asp-Lys-Thr-Asn-Glu-Phe | 40 | |
| 61 | | 80 | |
| 41 | Trp-Asn-Lys-Tyr-Lys-Asp-Gly-Asp-Gln-Cys-Glu-Thr-Ser-Pro-Cys-Gln-Asn-Gln-Gly-Lys | 60 | |
| 81 | | 100 | |
| 61 | Cys-Lys-Asp-Gly-Leu-Gly-Glu-Tyr-Thr-Cys-Thr-Cys-Leu-Glu-Gly-Phe-Glu-Gly-Lys-Asn | 80 | |
| 101 | | 120 | |
| 81 | Cys-Glu-Leu-Phe-Thr-Arg-Lys-Leu-Cys-Ser-Leu-Asp-Asn-Gly-Asp-Cys-Asp-Gln-Phe-Cys | 100 | |
| 121 | | 140 | |
| 101 | His-Glu-Glu-Gln-Asn-Ser-Val-Val-Cys-Ser-Cys-Ala-Arg-Gly-Tyr-Thr-Leu-Ala-Asp-Asn | 120 | |
| 141 | | 160 | |
| 121 | Gly-Lys-Ala-Cys-Ile-Pro-Thr-Gly-Pro-Tyr-Pro-Cys-Gly-Lys-Gln-ThrLeu-Glu-Arg-Arg | 140 | |
| 161 | | 180 | |
| 141 | Lys-Arg-Ser-Val-Ala-Gln-Ala-Thr-Ser-Ser-Ser-Gly-Glu-Ala-Pro-Asp-Ser-Ile-Thr-Trp | 160 | |
| 181 | | 200 | |
| 161 | Lys-Pro-Tyr-Asp-Ala-Ala-Asp-Leu-Asp-Pro-Thr-Glu-Asn-Pro-Phe-Asp-Leu-Leu-Asp-Phe | 180 | |
| 201 | | 220 | |
| 181 | Asn*-Gln-Thr-Gln-Pro-Glu-Arg-Gly-Asp-Asn-Asn*-Leu-Thr-Arg-Ile-Val-Gly-Gly-Gln-Glu | 200 | |
| 221 | | 240 | |
| 201 | Cys-Lys-Asp-Gly-Glu-Cys-Pro-Trp-Gln-Ala-Leu-Leu-Ile-Asn-Glu-Glu-Asn-Glu-Gly-Phe | 220 | |
| 241 | | 260 | |
| 221 | Cys-Gly-Gly-Thr-Ile-Leu-Ser-Glu-Phe-Tyr-Ile-Leu-Thr-Ala-Ala-His-Cys-Leu-Tyr-Gln | 240 | |
| 261 | | 280 | |
| 241 | Ala-Lys-Arg-Phe-Lys-Val-Arg-Val-Gly-Asp-Arg-Asn-Thr-Glu-Gln-Glu-Gly-Gly-Glu | 260 | |
| 281 | | 300 | |
| 261 | Ala-Val-His-Glu-Val-Glu-Val-Val-Ile-Lys-His-Asn-Arg-Phe-Thr-Lys-Glu-Thr-Tyr-Asp | 280 | |
| 301 | | 320 | |
| 281 | Phe-Asp-Ile-Ala-Val-Leu-Arg-Leu-Lys-Thr-Pro-Ile-Thr-Phe-Arg-Met-Asn-Val-Ala-Pro | 300 | |
| 321 | | 340 | |
| 301 | Ala-Cys-Leu-Pro-Glu-Arg-Asp-Trp-Ala-Glu-Ser-Thr-Leu-Met-Thr-Gln-Lys-Thr-Gly-Ile | 320 | |
| 341 | | 360 | |
| 321 | Val-Ser-Gly-Phe-Gly-Arg-Thr-His-Glu-Lys-Gly-Arg-Gln-Ser-Thr-Arg-Leu-Lys-Met-Leu | 340 | |
| 361 | | 380 | |
| 341 | Glu-Val-Pro-Tyr-Val-Asp-Arg-Asn-Ser-Cys-Lys-Leu-Ser-Ser-Ser-Phe-Ile-Ile-Thr-Gln | 360 | |
| 381 | | 400 | |
| 361 | Asn-Met-Phe-Cys-Ala-Gly-Tyr-Asp-Thr-Lys-Gln-Glu-Asp-Ala-Cys-Gln-Gly-Asp-Ser-Gly | 380 | |
| 401 | | 420 | |
| 381 | Gly-Pro-His-Val-Thr-Arg-Phe-Lys-Asp-Thr-Tyr-Phe-Val-Thr-Gly-Ile-Val-Ser-Trp-Gly | 400 | |
| 321 | | 440 | |
| 401 | Glu-Gly-Cys-Ala-Arg-Lys-Gly-Lys-Tyr-Gly-Ile-Tyr-Thr-Lys-Val-Thr-Ala-Phe-Leu-Lys | 420 | |
| 441 | | 460 | |
| 421 | Trp-Ile-Asp-Arg-Ser-Met-Lys-Thr-Arg-Gly-Leu-Pro-Lys-Ala-Lys-Ser-His-Ala-Pro-Glu | 440 | |
| 461 | | 430 | |
| 441 | Val-Ile-Thr-Ser-Ser-Pro-Leu-Lys | | |
| 481 | | | | mutated factor x polypeptides and uses thereof for the treatment of haemophilia

FIELD OF THE INVENTION

The present invention relates to mutated factor (FX) polypeptides and uses thereof for the treatment of haemophilia.

BACKGROUND OF THE INVENTION

Haemophilia A and B are inherited X-linked coagulopathies characterized by a lack of coagulation factor VIII (FVIII) and factor IX (FIX) respectively. Haemophilia A affects about 1 in 5 000 and Haemophilia B about 1 in 35 000 male births (1,2). Haemophilia leads to impaired thrombin generation, weak and vulnerable clots, and therefore spontaneous bleeding. Compared to severe patients, bleeding episodes are less frequent in moderate/mild patients, and are usually provoked by trauma or invasive procedures. Current treatment includes replacement therapy with recombinant or purified FVIII or FIX (3). However, one of the most serious drawbacks of these treatments is the development of alloantibodies, called inhibitors, inhibiting the activity of the coagulation factor, in a non-negligible number of patients with haemophilia A: 20-25% of severe patients and 7-13% of moderate/mild patients (4). Treatment of these inhibitor patients is limited to FVIII- or IX-bypassing agents, such as recombinant FVIIa (Novoseven®) or plasma-derived activated prothrombin complex (FEIBA®). However, these products have considerably shorter half-lives (4-7 h for FEIBA® and 1.5-2.7 h for Novoseven®), than the respective half-lives of FVIII (~12 h) and FIX (~18 h). These short half-lives require the need for frequent infusions, limiting the use of both products for prophylactic purposes and increasing the costs. They are expensive and a substantial number of patients do not respond to these agents.

Therefore, as an alternative therapeutic approaches, Factor X (FX) is a more attractive bypassing molecule, since it displays a 40 h half-life and is part of the coagulation cascade normally activated by both FVIII and FIX. For instance, a FX variant which combines activation of the molecule by thrombin with a long survival mimicking that of the FX zymogen was disclosed in WO 2010070137. This FX variant is activated without FVIII or FIX, in vitro as well as in vivo and could thus be used as a bypassing agent in both hemophilia A and B. However, the FX variants of the prior art are susceptible to inactivation due to the presence of inhibitors such as Antithrombin (AT) and/or the Tissue Pathway Inhibitor (TFPI). Actually, TFPI in complex with FXa (TFPI)-FXa inhibits the initiating complex of the coagulation Tissue Factor (TF)/FVIIa. TF/FVIIa complex initiates coagulation by activating FX. However, activation of FX to FXa by the FVIIIa/FIXa complex counteracts the activity of TFPI, allowing coagulation to proceed. In patients with haemophilia, the propagation phase of thrombin generation is not sustainable due to the lack of intrinsic tenase (FVIIIa/FIXa) complex (11). The limited availability of thrombin via TF-FVIIa pathway is in part due to rapid inhibition of FXa and thrombin by TFPI and AT (12, 13). In particular, plasma AT levels are normally high (2.6 µM), and AT is capable of inhibiting trace amounts of FXa and thrombin (13, 14). Therefore, a new upcoming strategy to treat coagulation disorders like hemophilia has recently emerged and implies neutralization of natural anticoagulants and especially TFPI and AT. This is based on several observations. Thus, low TFPI and AT levels in neonates are deemed to be important in augmenting thrombin generation with lower levels of procoagulant factors (15, 16). Furthermore, low AT levels improved haemostatic function in FVIII-deficient mice with heterozygous AT deficiency (17). Very recently, a biopharmaceutical company (Alnylam) developed an RNAi therapeutic targeting antithrombin (ALN-AT3) for the treatment of haemophilia and other rare bleeding disorders, which is currently being investigated in a multinational Phase 1 trial in haemophilia subjects. However, because of the high concentration of circulating plasma antithrombin (3-5 µM), targeting antithrombin via inhibitory molecules may not be the ideal way to obtain therapeutic attenuation of coagulation in haemophilia patients. For TFPI, different blocking reagents have been evaluated as possible therapeutic agents in different animal models with haemophilia (18, 19, 20, 21). However, there are some drawbacks for anti-TFPI agents. Indeed, TFPI is distributed among different pools: the major part is located in or at the endothelial surface, while the rest is distributed equally between platelets and plasma. Moreover, only 1% of total TFPI circulates as free protein in plasma, with the remainder bound to LDL-particles. Due to this complex biodistribution, it is difficult to monitor the efficacy of TFPI inhibition upon treatment in patient plasma samples. A second issue is that different splicing forms of TFPI are present (TFPIalpha and TFPIbeta), which act in different ways. Anti-TFPI based therapy should therefore be using agents that differentiate between both forms. To illustrate the difficulty to use the TFPI-blocking strategy, a clinical trial ran by Baxter using an aptamer directed against TFPI has been stopped due to an increased number of bleeding events. Biological explanations for this observation is that the blocking agent releases intracellularly stored TFPI, impacts its metabolism, and prolongs its circulatory half-life.

SUMMARY OF THE INVENTION

The present invention relates to mutated factor (FX) polypeptides and uses thereof for the treatment of haemophilia. In particular, the present invention is defined by the claims.

DETAILED DESCRIPTION OF THE INVENTION

The inventors now describe new FX polypeptides in which residues in the heavy chain were mutated at positions 215, 216, 218 from Glu (E) (FIG. 1) to Gln (Q). These selectively mutated residues on FX could thus interfere with the inhibition, when activated, by Antithrombin (AT) and/or the Tissue Pathway Inhibitor (TFPI). The inventors demonstrate that these molecules have the capacity to correct for the absence of FVIII or FIX in a calibrated thrombin generation assay with or without inhibitor. These properties give the proteins the potential to be used as bypassing agents in both haemophilia A and B, either episodically or prophylactically, and irrespective of the presence of inhibitors since calibrated thrombin generation assay has been shown to predict the response to bypassing agents (22).

A first object of the present invention relates to a mutated factor X (FX) polypeptide wherein the heavy chain comprises at least one mutation selected from the group consisting of:

- the mutation which consists of the substitution of the glutamic acid residue (E) at position 215 by a glutamine residue (Q), an asparagine residue (N), a serine residue (S), an alanine residue (A), or a tyrosine residue (Y);

the mutation which consists of the substitution of the glutamic acid residue (E) at position 216 by a glutamine residue (Q); and the mutation which consists of the substitution of the glutamic acid residue (E) at position 218 by a glutamine residue (Q);

As used herein, the term "factor X" has its general meaning in the art and refers to a secreted serine protease implicated in coagulation mechanisms. Typically, the amino acid sequence of the human factor X is provided by SEQ ID NO:1 (FIG. 1). The numbering systems used to localize the amino acid residues for factor X is based on the sequence deduced from the secreted protein, which contains the light chain, the activation peptide and the heavy chain: the amino acid residue numbered 1 is the first amino acid residue of the amino-terminal extremity of the light chain. As shown in FIG. 1, the sequence of factor X is divided in five different regions, which correspond, according to the used numbering system to:

the pre-peptide (or signal peptide) between the positions −40 to −28, the pro-peptide between the positions −27 to −1, the light chain between the positions 1 to 142 the activation peptide between the positions 143 to 194 the heavy chain between the position 195 to 448.

The signal peptide is cleaved off by signal peptidase, the propeptide sequence is cleaved off after gamma carboxylation took place at the first 11 glutamic acid residues at the N-terminus of the mature N-terminal chain. A further processing step occurs by cleavage between Arg142 and Ser143 according to the used numbering system (FIG. 1, positions 182-183 of SEQ ID NO:1). This processing step also leads concomitantly to the deletion of the tripeptide Arg140-Lys141-Arg142 (positions 180-182 of SEQ ID NO:1). The resulting secreted factor X zymogen consists of an N-terminal light chain of 139 amino acids and a C-terminal heavy chain of 306 amino acids which are covalently linked via a disulfide bridge between Cys132 and Cys302. As used herein, the term "activated Factor X" or "FXa" refers to the enzymatically active form of circulating factor X generated in case of coagulation activity (e.g. thrombin generation) is needed. Under physiological conditions able to activate factor X, the so called activation peptide of 52 amino acids from Ser143 to Arg194 is cleaved off the rest of the molecule by cleaving carboxy-terminal end of the heavy chain at Arg194 (FIG. 1). According to the numbering system of the present invention, the positions 215, 216 and 218 in Factor X corresponds respectively to positions 255, 256 and 258 in SEQ ID NO: 1.

As used herein, the term "substitution" means that a specific amino acid residue at a specific position is removed and another amino acid residue is inserted into the same position.

In some embodiments, the present invention relates to a mutated factor X (FX) polypeptide wherein the heavy chain comprises at least one mutation wherein the glutamic acid residue (E) at position 215, 216 or 218 is substituted by a glutamine residue (Q).

In some embodiments, the present invention relates to a mutated factor X (FX) polypeptide wherein the heavy chain comprises one mutation wherein the glutamic acid residue (E) at position 215 is substituted by a glutamine residue (Q).

In some embodiments, the present invention relates to a mutated factor X (FX) polypeptide wherein the heavy chain comprises one mutation wherein the glutamic acid residue (E) at position 216 is substituted by a glutamine residue (Q).

In some embodiments, the present invention relates to a mutated factor X (FX) polypeptide wherein the heavy chain comprises one mutation wherein the glutamic acid residue (E) at position 218 is substituted by a glutamine residue (Q).

In some embodiments, the mutated FX polypeptide of the present invention comprises a heavy chain which consists of the amino acid sequence having at least 90% of identity with the sequence ranging from the amino acid residue at position 195 to the amino acid residue at position 448 wherein at least one glutamic acid residue at position 215, 216 or 218 is mutated according to the invention. According to the invention a first amino acid sequence having at least 90% of identity with a second amino acid sequence means that the first sequence has 90; 91; 92; 93; 94; 95; 96; 97; 98; 99 or 100% of identity with the second amino acid sequence. In some embodiments, the mutated FX polypeptide of the invention comprises a heavy chain which consists of the amino acid sequence ranging from the amino acid residue at position 195 to the amino acid residue at position 448 wherein at least one glutamic acid residue at position 215, 216 or 218 is mutated according to the invention.

In some embodiments, the mutated FX polypeptide of the present invention comprises a heavy chain wherein the amino acid at position 196 is not substituted.

In some embodiments, the mutated FX polypeptide of the present invention further comprises a sequence cleavable by thrombin. In some embodiments, three amino acid of the activation peptide of FX (Thr-Arg-Ile) are substituted by Pro-Arg-Ala, thus, the mutated FX polypeptide constitutes a chimeric thrombin-cleavable derivative of factor X (as described in WO04005347). In some embodiments, the activation peptide of FX is substituted by fibrinopeptide A sequence, thus the mutated FX polypeptide constitutes a chimeric thrombin-cleavable derivative of factor X (as described in WO03035861). In some embodiments, the fibrinopeptide A sequence is inserted between the activation peptide and the heavy chain so that the mutated FX polypeptide constitutes a chimeric thrombin-cleavable derivative of factor X (as described in WO2010070137). As used herein, the term "fibrinopeptide A" has its general meaning in the art and refers to a small peptide of 16 amino acid residues removed from the N-terminal segment of the α-chain of fibrinogen by the action of thrombin. The amino acid sequence of the human fibrinopeptide A is provided by SEQ ID NO:2.

According to the invention, the mutated FX polypeptide of the invention is produced by conventional automated peptide synthesis methods or by recombinant expression. General principles for designing and making proteins are well known to those of skill in the art. The mutated FX polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The mutated FX polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art. As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides. A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, W138, and the like have specific cellular machinery and characteristic mechanisms for such post-translational activities and may be chosen to ensure the correct modification and processing of the introduced, foreign protein.

In specific embodiments, it is contemplated that the mutated FX polypeptides of the invention used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain. Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

A further object of the present invention relates to a nucleic acid molecule which encodes for a mutated FX polypeptide of the present invention.

As used herein, the term "nucleic acid molecule" has its general meaning in the art and refers to a DNA or RNA molecule. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

In some embodiments, the nucleic acid molecule of the present invention is included in a suitable vector, such as a plasmid, cosmid, episome, artificial chromosome, phage or a viral vector. So, a further object of the invention relates to a vector comprising a nucleic acid encoding for a mutated FX polypeptide of the invention. Typically, the vector is a viral vector which is an adeno-associated virus (AAV), a retrovirus, bovine papilloma virus, an adenovirus vector, a lentiviral vector, a vaccinia virus, a polyoma virus, or an infective virus. In some embodiments, the vector is an AAV vector. As used herein, the term "AAV vector" means a vector derived from an adeno-associated virus serotype, including without limitation, AAV1, AAV2, AAV3, AAV4, AAV5, AAV6, AAV7, AAV8, AAV9, and mutated forms thereof. AAV vectors can have one or more of the AAV wild-type genes deleted in whole or part, preferably the rep and/or cap genes, but retain functional flanking ITR sequences. Retroviruses may be chosen as gene delivery vectors due to their ability to integrate their genes into the host genome, transferring a large amount of foreign genetic material, infecting a broad spectrum of species and cell types and for being packaged in special cell-lines. In order to construct a retroviral vector, a nucleic acid encoding a gene of interest is inserted into the viral genome in the place of certain viral sequences to produce a virus that is replication-defective. In order to produce virions, a packaging cell line is constructed containing the gag, pol, and/or env genes but without the LTR and/or packaging components. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HIV 1, HIV 2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are known in the art, see, e.g. U.S. Pat. Nos. 6,013,516 and 5,994,136, both of which are incorporated herein by reference. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest. Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species. Typically, the nucleic acid molecule or the vector of the present invention include "control sequences", which refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Another nucleic acid sequence, is a "promoter" sequence, which is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

A further object of the present invention relates to a host cell transformed with the nucleic acid molecule of the present invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". In a particular embodiment, for expressing and producing the mutated FX polypeptides of the present invention, prokaryotic cells, in particular E. Coli cells, will be chosen. Actually, according to the invention, it is not mandatory to produce the mutated FX polypeptides of the present invention in a eukaryotic context that will favour post-translational modifications (e.g. glycosylation). Furthermore, prokaryotic cells have the advantages to produce protein in large amounts. If a eukaryotic context is needed, yeasts (e.g. *saccharomyces* strains) may be particularly suitable since they allow production of large amounts of proteins. Otherwise, typical eukaryotic cell lines such as CHO, BHK-21, COS-7, C127, PER.C6, YB2/0 or HEK293 could be used, for their ability to process to the right post-translational modifications of the mutated FX polypeptides of the present invention. The construction of expression vectors in accordance with the invention, and the transformation of the host cells can be carried out using conventional molecular biology techniques. The mutated FX polypeptide of the invention, can, for example, be obtained by culturing genetically transformed cells in accordance with the invention and recovering the mutated FX polypeptide expressed by said cell, from the culture. They may then, if necessary, be purified by conventional procedures, known in themselves to those skilled in the art, for example by fractional precipitation, in particular ammonium sulfate precipitation, electrophoresis, gel filtration, affinity chromatography, etc. In particular, conventional methods for preparing and purifying recombinant proteins may be used for producing the proteins in accordance with the invention.

The mutated FX polypeptides of the present invention and nucleic acid molecules encoding thereof are typically used as medicament. In particular, the nucleic acid molecules of the present invention (inserted or not into a vector) are particularly suitable for gene therapy. In some embodiments, the mutated FX polypeptides of the present invention and nucleic acid molecules (inserted or not into a vector) are particularly suitable for the treatment of haemophilia. Haemophilia includes haemophilias A or B, which may or may not be complicated by the presence of inhibitors (neutralizing allo-antibodies directed against the factor VIII or IX conventionally used for treatment); they may also be acquired haemophilias resulting from the appearance of auto antibodies associated with another pathology (autoimmune disease, cancer, lymphoproliferative syndrome, idiopathic disorder, etc.).

Accordingly a further object of the present invention relates to a method for treating haemophilia in a subject in need thereof comprising administering the subject with a therapeutically effective amount of a mutated FX polypeptide of the present invention or a nucleic acid molecule of the present invention which is inserted or not in to a vector as above described.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

By a "therapeutically effective amount" is meant a sufficient amount of the mutated FX polypeptide or the nucleic acid molecule encoding thereof to prevent for use in a method for the treatment of the disease (e.g. haemophilia) at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the mutated FX polypeptide or the nucleic acid molecule (inserted or not into a vector) of the present invention is administered to the subject in the form of a pharmaceutical composition. Typically, the mutated FX polypeptide or the nucleic acid molecule (inserted or not into a vector) of the present invention may be combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The mutated FX polypeptide or the nucleic acid molecule (inserted or not into a vector) of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1: Schematic representation of different parts of factor X zymogen amino acid sequence. The pre-peptide (or signal peptide) is defined by the amino acid sequence between the positions −40 to −18 and the pro-peptide by the amino acid sequence between the positions −17 to −1. The light chain corresponds to the sequence between the amino acid positions 1 to 142 and the heavy chain between amino acid positions 195 to 448. The activation peptide (positions 143 to 194) is boxed and N-glycosylation sites of interest are tagged by an *. The numbering system used appears on the same line as the sequence and the other reference system appears in grey on the line under the sequence.

EXAMPLE

Material & Methods

Engineering and Production of Recombinant FX and FX Derivatives cDNAs encoding wild-type (wt)-human FX (wt-hFX), and its variants FXE215Q, FXE216Q and FXE218Q (FIG. 1) were synthetically synthesized (Eurofins, Ebersberg Germany) and cloned in expression vectors using standard molecular biological protocols. Constructs were cloned into the pLIVE- and pNUT-plasmids for in vivo expression and in vitro expression in stably transfected in BHK-21 cells, respectively (23, 24, 25). All constructs contained a DNA sequence encoding the epitope recognized by antibody HPC4 (Roche, Meylan, France) that was added at the 3' end of the FX sequence. Stable BHK-21 cell lines producing FX or variants thereof were established as described (25) and detailed in the following section.

Obtention of Cell Lines Expressing the Recombinant Derivatives

The pNUT-constructs were transfected into Baby hamster kidney cells (BHK) using the jetPEI reactant (Qbiogen, Ozyme, France) as specified by the provider. After selection of transfected cells with medium containing methotrexate (Sigma) at a concentration of 100 µM, single clones were picked and propagated in selective medium to obtain stable cell lines. Production of factor X antigen was assayed by enzyme-linked immunosorbent assay (ELISA) using polyclonal antibodies against factor X conjugated and not with horseradish peroxidase obtained from Cederlane (Cederlane Laboratories, Burlington, Canada). Purified human plasma derived factor X (pd-FX) from Cryopep (Montepellier, France) was used as reference.

Production and Purification of Recombinant Factor X and Derivatives

Stable cell lines producing recombinant factor X, and were maintained in 300 cm2 flasks for protein production in DMEM/F-12 supplemented with 10% FCS, 50 µM methotrexate, 100 U/ml penicillin, 100 µg/ml streptomycin, and 5 µg/ml vitamin K1. Protein of interest containing medium was harvested every 48 hours. Benzamidine and PMSF were added to a final concentration of 10 and 2 mM, respectively, and the medium centrifuged (6 000 g), passed over cellulose acetate membranes (0.45 µm) to eliminate cell debris, and stored at −20° C. until use. Conditioned medium was thawed at 37° C. EDTA was added to a final concentration of 5 mM. The medium was diluted in distilled water and in Tris (pH 7.4), to bring the final Tris and NaCl concentration to 25 and 60 mM, respectively. The mixture was then stirred at room temperature for 30 min with QAE Sephadex A-50 beads to achieve a final concentration of 0.25% (wt/v). Beads were washed before elution with 50 mM Tris (pH 7.4), 500 mM NaCl, and 10 mM benzamidine. Recombinant proteins contained in the eluted fractions (ELISA) were immediately dialyzed against 25 mM Tris (pH 7.4), and 100 mM NaCl, containing 10 mM benzamidine, and stored at −20° C. before use. Concentrated proteins were thawed at 37° C. Calcium was added to a final concentration of 5 mM. Purification of recombinant proteins was performed by affinity-chromatography using HPC-4-agarose (Roche, Meylan, France) as instructed by the provider. 1 h prior to use as a zymogen, factor X derivatives were incubated with 1 mM PMSF to neutralize any trace of activated factor X that may have been generated during production or purification of the recombinant protein. Control experiments indicated that after 30 min in Tris-HCl buffer, PMSF was fully hydrolyzed and would not interfere with other reactions. Protein purity was assessed using 10% SDS-polyacrylamide gel electrophoresis analysis of the recombinant proteins under reducing (100 mM dithiothreitol, final concentration) and non-reducing conditions followed by staining with Coomassie Brilliant Blue R-250. Factor X identification was carried out after the purified recombinant proteins were reduced and loaded onto a 10% SDS-polyacrylamide gel. The resolved proteins were transferred to an Immobilon membrane and blotted using polyclonal antibodies against factor X conjugated with horseradish peroxydase (Cederlane). The purified derivatives were aliquoted and stored at −80° C. until use. The concentration of the aliquot is estimated by its absorbance at 280 nm, taking 1.16 to be the extinction coefficient (E280 nm 0.1%) of factor X.

Thrombin Generation Assay

Thrombin generation was measured according to the method described by Hemker et al (26), in a Fluoroscan Ascent fluorometer (Thermolabsystems OY, Helsink, Finland) equipped with a dispenser. Briefly, 80 µl of plasma supplemented with either saline (control) or with indicated concentration of recombinant factor X derivatives were dispensed into round-bottom 96-well microtiter plates. Twenty µl of a mixture containing TF (recombinant lipidated human tissue factor, Innovin®, obtained from Dade Behring) and phospholipids (PL) vesicles was added to the plasma sample to obtain a final concentration of 1 pM TF and 4 µM PL vesicles. PL vesicles prepared from L-α-Phosphatidyl-L-serine (PS) L-α-phosphatidylethanolamine (PE) and L-α-phosphatidylcholine (PC) (Avanti Polarlipids, Alabaster, Ala., USA) and of nominal 100 nm-diameter (PC:PE:PS, 3:1:1) were synthesized by the method of membrane extrusion (27). Phospholipid concentration was determined by phosphate analysis. Finally, thrombin generation was triggered by adding 20 µl of starting reagent containing fluorogenic substrate and $CaCl_2$. Fluorogenic substrate 1-1140 (Z-Gly-Gly-Arg-AMC) was from Bachem AG (Bubendorf, Switzerland). Kinetics of thrombin generation in clotting plasma was monitored for 60 min at 37° C. using a calibrated automated thrombogram and analyzed using the Thrombinoscope™ software (Thrombinoscope B.V., Maastricht, the Netherlands). Four wells were needed for each experiment, two wells to measure thrombin generation of a plasma sample and two wells for calibration. All experiments were carried out in triplicate and the mean value was reported. Endogenous thrombin potential (ETP), i.e. area under the curve, peak thrombin, and lag time for thrombin detection determined. In some experiments, immunodepleted FVIII-plasma (Diagnostica Stago, Asnieres, France) was supplemented with FX variants (60, 150 and 300 nM final concentrations) or recombinant purified FVIII (0.025, 0.1, and 1 U/ml Kogenate® FS, Bayer HealthCare, Puteaux, France). In other experiments, immunodepleted FVIII-deficient human plasma was supplemented with mouse monoclonal anti-FVIII antibody D4H1 to create FVIII-inhibitor plasma (28). D4H1 at a final concentration of 10 µg/ml or 50 µg/ml corresponds to 30-40 Bethesda Units (BU)/ml and 150-200 BU, respectively. Subsequently, FVIII inhibitor plasma was supplemented in vitro with various concentrations FX derivatives. Finally, experiments were performed using immunodepleted FIX-plasma (Diagnostica Stago, Asnieres, France).

Results:

Thrombin Generation in FVIII and FIX-Deficient Plasmas

In a first series of experiments, we assessed the potential of different concentrations of FVIII, 1, 0.1, and 0.025 U/ml corresponding to a normal individual (control), a mild and a moderate hemophilia, respectively, to compensate for the absence of FVIII in the generation of thrombin. To this end, coagulation in immunodepleted FVIII-deficient human plasma was initiated by the addition of TF (1 pM) and phospholipids (4 µM), and relevant thrombin generation parameters such as ETP and peak thrombin generation were determined. In the absence of any added coagulation factor, this resulted in an ETP and a peak thrombin generation (for summary see Table 1). Both values are significantly reduced compared to normal plasma (ETP: ~1200 nM·min; peak thrombin generation: 150-174 nM). As expected, the addition of FX derivatives (60, 150, 200 and 300 nM final concentrations) resulted in restoration of thrombin generation in FVIII-deficient plasma (Table 1). Also the addition of FXE215Q, FXE216Q or FXE218Q to a concentration of 300 nM resulted in normalization of thrombin generation, with both ETP and peak thrombin generation being within the same range as found for normal plasma (Table 1). A similar correction of the coagulation defect was observed when tested in immunodepleted FIX-deficient plasma (Table 2). Furthermore, no correction of thrombin generation was observed by the addition of wt-FX up to the highest concentration tested (0.5 µM). These data indicate that under the conditions employed, the presence of the mutation gives the capacity to FX to overcome the absence of FVIII or FIX for efficient thrombin generation.

Thrombin Generation in FVIII-Deficient Inhibitor Plasma

We next evaluated FX derivatives for their ability to correct the coagulation deficiency in FVIII-deficient plasma in the presence of anti-FVIII antibody 4D1, dosed at a concentration of 150 BU/ml. The addition of increasing concentration FX derivatives resulted in normalization of the total thrombin generation (Table 3). Thus, the FXE215Q, FXE216Q or FXE218Q appears to be an efficient procoagulant agent to correct thrombin generation in FVIII-inhibitor plasma.

Tables:

TABLE 1

Thrombin generation test in FVIII-deficient plasma (Cryopep, Montpellier). Parameters for measuring thrombin generation (ETP, thrombin peak) were measured in immunodepleted FVIII-deficient plasma in the presence of tissue factor (1 pM) and phospholipids (4 µM) with or without FVIII, FXE215Q, FXE216Q or FXE218Q. Data are presented as mean ± SD.

| Added coagulation factor in FVIII-deficient plasma | n | ETP (nM · min) | Thrombin Peak (nM) |
|---|---|---|---|
| FVIII (1 U/ml) | 7 | 815 ± 52 | 179 ± 8 |
| FVIII (0.1 U/ml) | 6 | 634 ± 31 | 56 ± 5 |
| FVIII (0.025 U/ml) | 6 | 441 ± 38 | 28 ± 3 |
| None | 7 | 213 ± 27 | 11 ± 1 |
| FXE215Q (300 nM) | 3 | 835 ± 35 | 156 ± 7 |
| FXE215Q (150 nM) | 3 | 762 ± 96 | 66 ± 5 |
| FXE215Q (60 nM) | 3 | 558 ± 43 | 39 ± 2 |
| FXE216Q (200 nM) | 3 | 795 ± 25 | 119 ± 5 |
| FXE218Q (300 nM) | 3 | 856 ± 40 | 139 ± 4 |
| FXE218Q (150 nM) | 3 | 771 ± 45 | 58 ± 4 |
| FXE218Q (60 nM) | 3 | 297 ± 28 | 18 ± 1 |

TABLE 2

Thrombin generation test in FIX-immunodepleted plasma (Stago, France). Parameters for measuring thrombin generation (ETP, thrombin peak) were measured in immunodepleted FIX-deficient plasma in the presence of tissue factor (1 pM) and phospholipids (4 µM) with or without FIX, FXE215Q, FXE216Q or FXE218Q. Data are presented as mean ± SD.

| Added coagulation factor in FIX-deficient plasma | n | ETP (nM · min) | Thrombin Peak (nM) |
|---|---|---|---|
| FIX (1 U/ml) | 3 | 1356 ± 30 | 295 ± 8 |
| FIX (0.1 U/ml) | 3 | 802 ± 19 | 81 ± 5 |
| FIX (0.025 U/ml) | 3 | 424 ± 18 | 29 ± 1 |
| None | 3 | 239 ± 68 | 10 ± 3 |
| FXE215Q (300 nM) | 3 | 1019 ± 17 | 223 ± 3 |
| FXE215Q (150 nM) | 3 | 892 ± 30 | 49 ± 4 |
| FXE215Q (60 nM) | 3 | 467 ± 12 | 21 ± 4 |
| FXE216Q (200 nM) | 3 | 787 ± 22 | 121 ± 5 |
| FXE218Q (300 nM) | 3 | 1188 ± 17 | 294 ± 8 |
| FXE218Q (150 nM) | 3 | 993 ± 23 | 81 ± 4 |
| FXE218Q (60 nM) | 3 | 491 ± 20 | 29 ± 4 |

TABLE 3

Thrombin generation test in FVIII-deficient plasma (Cryopep, Montpellier) in the presence of inhibitor. Parameters for measuring thrombin generation (ETP, thrombin peak) were measured in FVIII-deficient plasma supplemented with mouse monoclonal anti-FVIII antibody D4H1 to create FVIII-inhibitor plasma in the presence of tissue factor (1 pM) and phospholipids (4 µM) with or without FVIII, FXE215Q, FXE216Q or FXE218Q. Data are presented as mean ± SD.

| Added coagulation factor in FVIII-deficient plasma supplemented with inhibitor | n | ETP (nM · min) | Thrombin Peak (nM) |
|---|---|---|---|
| FXE215Q (300 nM) | 3 | 978 ± 41 | 101 ± 6 |
| FXE215Q (150 nM) | 3 | 536 ± 20 | 48 ± 4 |
| FXE215Q (60 nM) | 3 | 306 ± 15 | 17 ± 4 |
| FXE215Q (30 nM) | 3 | 208 ± 11 | 8 ± 4 |
| FXE216Q (200 nM) | 3 | 685 ± 20 | 54 ± 4 |
| FXE218Q (300 nM) | 3 | 949 ± 41 | 113 ± 4 |
| FXE218Q (150 nM) | 3 | 643 ± 11 | 64 ± 4 |
| FXE218Q (60 nM) | 3 | 418 ± 9 | 24 ± 2 |
| FXE218Q (30 nM) | 3 | 276 ± 13 | 14 ± 1 |

SEQUENCES

```
SEQ ID NO: 1: Factor X (homo sapiens)
MGRPLHLVLL SASLAGLLLL GESLFIRREQ ANNILARVTR

ANSFLEEMKK GHLERECMEE TCSYEEAREV FEDSDKTNEF

WNKYKDGDQC ETSPCQNQGK CKDGLGEYTC TCLEGFEGKN

CELFTRKLCS LDNGDCDQFC HEEQNSVVCS CARGYTLADN

GKACIPTGPY PCGKQTLERR KRSVAQATSS SGEAPDSITW

KPYDAADLDP TENPFDLLDF NQTQPERGDN NLTRIVGGQE

CKDGECPWQA LLINEENEGF CGGTILSEFY ILTAAHCLYQ

AKRFKVRVGD RNTEQEEGGE AVHEVEVVIK HNRFTKETYD

FDIAVLRLKT PITFRMNVAP ACLPERDWAE STLMTQKTGI

VSGFGRTHEK GRQSTRLKML EVPYVDRNSC KLSSSFIITQ

NMFCAGYDTK QEDACQGDSG GPHVTRFKDT YFVTGIVSWG

EGCARKGKYG IYTKVTAFLK WIDRSMKTRG LPKAKSHAPE

VITSSPLK

SEQ ID NO: 2: fibrinopeptide A (homo sapiens)
ADSGEGDFLA EGGGVR
```

REFERENCES

Throughout this application, various references describe the state of the art to which this invention pertains. The disclosures of these references are hereby incorporated by reference into the present disclosure.

1 Stonebraker J S, Bolton-Maggs P H, Michael Soucie J, Walker I, Brooker M. A study of variations in the reported haemophilia B prevalence around the world. Haemophilia. 2012; 18(3):e91-94.
2 Stonebraker J S, Bolton-Maggs P H, Soucie J M, Walker I, Brooker M. A study of variations in the reported haemophilia A prevalence around the world. Haemophilia. 2010; 16(1):20-32.
3 Berntorp E, Shapiro A D. Modern haemophilia care. Lancet. 2012; 379(9824):1447-1456.
4. Witmer C, Young G. Factor VIII inhibitors in hemophilia A: rationale and latest evidence. Therapeutic advances in hematology. 2013; 4(1):59-72.
5 Louvain-Quintard V B, Bianchini E P, Calmel-Tareau C, Tagzirt M, Le Bonniec B F. Thrombin-activable factor X re-establishes an intrinsic amplification in tenase-deficient plasmas. J Biol Chem. 2005; 280(50):41352-41359.
6 Bunce M W, Toso R, Camire R M. Zymogen-like factor Xa variants restore thrombin generation and effectively bypass the intrinsic pathway in vitro. Blood. 2011; 117(1):290-298.
7 Ivanciu L, Toso R, Margaritis P, et al. A zymogen-like factor Xa variant corrects the coagulation defect in hemophilia. Nature biotechnology. 2011; 29(11):1028-1033.
8 Gueguen P, Cherel G, Badirou I, Denis C V, Christophe O D. Two residues in the activation peptide domain contribute to the half-life of factor X in vivo. J Thromb Haemostas. 2010; 8(7):1651-1653.
9 Kurdi M, Cherel G, Lenting P J, Denis C V, Christophe O D. Coagulation factor X interaction with macrophages through its N-glycans protects it from a rapid clearance. PloS one. 2012; 7(9):e45111.
10 Johansson L, Karpf D M, Hansen L, Pelzer H, Persson E. Activation peptides prolong the murine plasma half-life of human factor VII. Blood. 2011; 117(12):3445-3452.
11 Tanaka K A, Key N S, Levy J H. Blood coagulation: hemostasis and thrombin regulation. Anesth Analg 2009; 108: 1433-1446.
12 Baugh R J, Broze G J, Jr., Krishnaswamy S. Regulation of extrinsic pathway factor Xa formation by tissue factor pathway inhibitor. J Biol Chem 1998; 273: 4378-4386.
13 Lu G, Broze G J, Jr., Krishnaswamy S. Formation of factors IXa and Xa by the extrinsic pathway: differential regulation by tissue factor pathway inhibitor and antithrombin III. J Biol Chem 2004; 279: 17241-17249.
14 Jesty J, Beltrami E. Positive feedbacks of coagulation: their role in threshold regulation. Arterioscler Thromb Vasc Biol 2005; 25: 2463-2469.
15 Cvirn G, Gallistl S, Leschnik B, et al. Low tissue factor pathway inhibitor (TFPI) together with low antithrombin allows sufficient thrombin generation in neonates. J Thromb Haemost 2003; 1: 263-268.

16 Fritsch P, Cvirn G, Cimenti C, et al. Thrombin generation in factor VIII-depleted neonatal plasma: nearly normal because of physiologically low antithrombin and tissue factor pathway inhibitor. J Thromb Haemost 2006; 4: 1071-1077.

17 Bolliger D, Szlam F, Suzuki N, Matsushita T, Tanaka K A. Heterozygous antithrombin deficiency improves in vivo haemostasis in factor VIII-deficient mice. Thromb Haemost 201; 1233-1238

18 Hilden I, Lauritzen B, Sorensen B B, Clausen J T, Jespersgaard C, Krogh B O, Bowler A N, Breinholt J, Gruhler A, Svensson L A, Petersen H H, Petersen L C, Balling K W, Hansen L, Hermit M B, Egebjerg T, Friederichsen B, Ezban M, Bjorn S E. Hemostatic effect of a monoclonal antibody mAb 2021 blocking the interaction between FXa and TFPI in a rabbit hemophilia model. Blood. 2012; 119: 5871-8.

19 Prasad S, Lillicrap D, Labelle A, Knappe S, Keller T, Burnett E, Powell S, Johnson K W. Efficacy and safety of a new-class hemostatic drug candidate, AV513, in dogs with hemophilia A. Blood. 2008; 111: 672-9.

20 Waters E K, Genga R M, Schwartz M C, Nelson J A, Schaub R G, Olson K A, Kurz J C, McGinness K E. Aptamer ARC19499 mediates a procoagulant hemostatic effect by inhibiting tissue factor pathway inhibitor. Blood. 2011; 117: 5514-22.

21 Maroney S A, Cooley B C, Ferrel J P, Bonesho C E, Nielsen L V, Johansen P B, Hermit M B, Petersen L C, Mast A E. Absence of hematopoietic tissue factor pathway inhibitor mitigates bleeding in mice with hemophilia. Proceedings of the National Academy of Sciences of the United States of America. 2012; 109: 3927-31.

22 Young G, Sorensen B, Dargaud Y, Negrier C, Brummel-Ziedins K, Key N S. Thrombin generation and whole blood viscoelastic assays in the management of hemophilia: current state of art and future perspectives. Blood. 2013; 121(11):1944-1950.

23 Christophe O D, Lenting P J, Cherel G, et al. Functional mapping of anti-factor IX inhibitors developed in patients with severe hemophilia B. Blood. 2001; 98(5):1416-1423.

24 Marx I, Christophe O D, Lenting P J, et al. Altered thrombus formation in von Willebrand factor-deficient mice expressing von Willebrand factor variants with defective binding to collagen or GPIIbIIIa. Blood. 2008; 112(3):603-609.

25 Levigne S, Thiec F, Cherel G, Irving J A, Fribourg C, Christophe O D. Role of the alpha-helix 163-170 in factor Xa catalytic activity. J Biol Chem. 2007; 282(43):31569-31579.

26 Hemker H C, Giesen P, Al Dieri R, et al. Pathophysiol Haemost Thromb 2003; 33:4-15.

27 Olson, F., Hunt, C. A., Szoka, F. C., Vail, W. J., and Papahadjopoulos, D. (1979) Biochim Biophys Acta 557 (1), 9-23.

28 Girma J P, Fressinaud E, Houllier A, Laurian Y, Amiral J, Meyer D. Assay of factor VIII antigen (VIII:CAg) in 294 haemophilia A patients by a new commercial ELISA using monoclonal antibodies. Haemophilia. 1998; 4(2): 98-103.

The invention claimed is:

1. A mutated factor X (FX) polypeptide comprising a heavy chain comprising the amino acid sequence of SEQ ID NO:1 from the amino acid residue at position 235 to the amino acid residue at position 488 of SEQ ID NO: 1, wherein the heavy chain comprises at least one mutation selected from the group consisting of:
   a mutation comprising substitution of a glutamic acid residue (E) at position 255 by a glutamine residue (Q), a serine residue (S), an alanine residue (A), or a tyrosine residue (Y);
   a mutation comprising substitution of a glutamic acid residue (E) at position 256 by a glutamine residue (Q); and
   a mutation comprising substitution of a glutamic acid residue (E) at position 258 by a glutamine residue (Q),
   wherein the at least one mutation is a glutamine residue at position 255, 256, or 258.

2. The mutated factor X (FX) polypeptide of claim 1 wherein the heavy chain comprises at least one mutation wherein the glutamic acid residue (E) at position 255 is substituted by a glutamine residue (Q).

3. The mutated factor X (FX) polypeptide of claim 1 wherein the heavy chain comprises at least one mutation wherein the glutamic acid residue (E) at position 256 is substituted by a glutamine residue (Q).

4. The mutated factor X (FX) polypeptide of claim 1 wherein the heavy chain comprises at least one mutation wherein the glutamic acid residue (E) at position 258 is substituted by a glutamine residue (Q).

5. A pharmaceutical composition which comprises the mutated factor X (FX) polypeptide of claim 1.

6. A mutated factor X (FX) polypeptide comprising a heavy chain comprising the amino acid sequence of SEQ ID NO:1 from the amino acid residue at position 235 to the amino acid residue at position 488 of SEQ ID NO: 1, wherein the heavy chain comprises at least one mutation selected from the group consisting of:
   a mutation comprising substitution of a glutamic acid residue (E) at position 255 by a glutamine residue (Q), a serine residue (S), an alanine residue (A), or a tyrosine residue (Y);
   a mutation comprising substitution of a glutamic acid residue (E) at position 256 by a glutamine residue (Q); and
   a mutation comprising substitution of a glutamic acid residue (E) at position 258 by a glutamine residue (Q).

7. A pharmaceutical composition which comprises the mutated factor X (FX) polypeptide of claim 6.

8. A mutated factor X (FX) polypeptide comprising a heavy chain comprising the amino acid sequence of SEQ ID NO:1 from the amino acid residue at position 235 to the amino acid residue at position 488 of SEQ ID NO: 1, wherein the heavy chain comprises at least one mutation selected from the group consisting of:
   a mutation comprising substitution of a glutamic acid residue (E) at position 255 by a glutamine residue (Q), a serine residue (S), an alanine residue (A), or a tyrosine residue (Y);
   a mutation comprising substitution of a glutamic acid residue (E) at position 256 by a glutamine residue (Q); and
   a mutation comprising substitution of a glutamic acid residue (E) at position 258 by a glutamine residue (Q),
   wherein the FX polypeptide comprises an activation peptide and wherein a fibrinopeptide A is inserted between the activation peptide and the heavy chain.

9. The mutated factor X (FX) polypeptide of claim 8 wherein the fibrinopeptide A comprises the amino acid sequence of SEQ ID NO:2.

10. A pharmaceutical composition which comprises the mutated factor X (FX) polypeptide of claim 8.

\* \* \* \* \*

SEQUENCE LISTING

```
<160> NUMBER OF SEQ ID NOS: 2

<210> SEQ ID NO 1
<211> LENGTH: 488
<212> TYPE: PRT
<213> ORGANISM: Homo sapiens

<400> SEQUENCE: 1

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
```

```
                         165                 170                 175
Leu Glu Arg Arg Lys Arg Ser Val Ala Gln Ala Thr Ser Ser Ser Gly
                180                 185                 190

Glu Ala Pro Asp Ser Ile Thr Trp Lys Pro Tyr Asp Ala Ala Asp Leu
            195                 200                 205

Asp Pro Thr Glu Asn Pro Phe Asp Leu Leu Asp Phe Asn Gln Thr Gln
        210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 2
<211> LENGTH: 16
<212> TYPE: PRT
<213> ORGANISM: Homo sapiens

<400> SEQUENCE: 2

Ala Asp Ser Gly Glu Gly Asp Phe Leu Ala Glu Gly Gly Gly Val Arg
1               5                   10                  15
```